United States Patent
Pipino

(10) Patent No.: US 6,922,459 B2
(45) Date of Patent: Jul. 26, 2005

(54) X-RAY INSPECTION DEVICE FOR FOOD PRODUCTS

(75) Inventor: Marco Pipino, Chivasso (IT)

(73) Assignee: Dylog Italia S.p.A., Turin (IT)

( * ) Notice: Subject to any disclaimer, the term of this patent is extended or adjusted under 35 U.S.C. 154(b) by 86 days.

(21) Appl. No.: 10/297,564

(22) PCT Filed: Jun. 8, 2001

(86) PCT No.: PCT/IB01/01015

§ 371 (c)(1),
(2), (4) Date: Jun. 11, 2003

(87) PCT Pub. No.: WO01/94923

PCT Pub. Date: Dec. 13, 2001

(65) Prior Publication Data

US 2004/0028177 A1 Feb. 12, 2004

(30) Foreign Application Priority Data

Jun. 9, 2000 (IT) ...................................... TO2000A0555

(51) Int. Cl.[7] .............................................. G01N 23/04
(52) U.S. Cl. .......................................... 378/57; 378/58
(58) Field of Search ............................. 378/57, 51, 56, 378/58; 250/358.1, 359.1, 360.1, 559.09, 559.12, 559.15, 223 B, 559.4, 559.06; 356/239.4, 239.5, 239.6

(56) References Cited

U.S. PATENT DOCUMENTS

| 4,366,382 A | 12/1982 | Kotowski |
| 5,216,239 A | 6/1993 | Yoshida |
| 5,602,890 A | * 2/1997 | Gray et al. ................... 378/57 |
| 5,917,880 A | 6/1999 | Bjorkholm |

FOREIGN PATENT DOCUMENTS

| DE | 19823448 | 11/1999 |
| EP | 0 449 113 A2 | 10/1991 |
| EP | 0 184 247 | 6/1996 |
| EP | 0 795 746 A1 | 9/1997 |
| GB | 2 329 817 A | 3/1999 |
| WO | WO 98/33062 | 7/1998 |

OTHER PUBLICATIONS

Evan et al., Design of a Stereoscopic X–ray Imaging System using a Single X–ray Source, NDT&E international 33, entire document.*

Evans J P O et al: Design Of A Stereoscopic X–Ray Imaging System Using A Single X–Ray Source:May 4, 1999: pp. 325 and 332.

* cited by examiner

Primary Examiner—David V. Bruce
Assistant Examiner—Hoon Song
(74) Attorney, Agent, or Firm—Paul & Paul

(57) ABSTRACT

A device for non-destructive inspection of containers (22) of food products comprises an emitter (24) emitting a divergent radiation beam, with vertical axis and a pair of detectors (26) detecting the radiation coming from the emitter (24) and passing through a container (22) to be inspected; the radiation detectors (28, 30) are linear detectors and are spaced so as to receive radiation (32, 32') emitted by the emitter (24) according to two different directions.

7 Claims, 4 Drawing Sheets

X-RAY INSPECTION DEVICE FOR FOOD PRODUCTS

The present invention relates to an X-ray inspection device.

More particularly, the invention relates to a device for non-destructive inspection of containers of food products.

It is known that non-destructive X-ray inspection of containers of food products is carried out by stationary inspection apparatuses inside which the containers to be inspected are made to pass on a horizontal conveyor belt. Said apparatuses comprise an X-ray emitter connected with a suitable detector, and the relevant control circuits.

Inspection of containers of food products aims at detecting the presence of possible contaminants within the container. Indeed, it is possible that during the working and bottling phases a particle or fragment of a foreign substance, generally of higher specific weight than the liquid where it is by chance present, is found within the container.

It is known that in most cases non-destructive X-ray inspection of glass containers for food industry is carried out by individual apparatuses, located aside the row of said containers to be inspected. Said apparatuses are substantially equipped with an emitter and a detector between which the row of said containers to be inspected passes.

It is also known that said individual apparatuses result in an inspection of 90 to 95% the contained product, said limitation being due to shadow areas created by concavities or inclined walls in the container.

In many cases said result has been wrongly considered sufficient. In effect, a 95% validity only of the inspection has created several problems. Some attempts to remedy such problems have been made, which however were rather complex and expensive, and scarcely satisfactory.

Among such attempts it is worthwhile mentioning the solution proposed in Italian Patent 1 285 008 in the name of the same Applicant, which discloses a side inspection apparatus for glass containers and/or cares for food industry. Said apparatus comprises a static structure consisting of two modular units arranged at 90° relative to each ether and at 45° relative to the container displacement line. One unit is equipped with a semi-panoramic emitter and a detector, whereas the other unit is equipped with a detector only, identical to that of the first unit.

Such a solution allowed eliminating some shadow areas due for instance to the curvature of the container bottoms. Yet it does not allow a direct inspection of the container bottom, that is of the region where contaminants become deposited.

It is therefore an object of the present invention to obviate the above drawbacks, by providing a method of using an inspection device allowing a complete and direct inspection, in quick and sure manner, of the bottom of a glass or metal container.

The above and other objects are achieved by a method of using a device for non-destructive X-ray inspection of containers of liquid products, such as glass jars or pots, in accordance with the invention, as claimed in the appended claims.

The method of the invention uses an inspection device with a vertically arranged radiation emitter and at least two radiation detectors, located close to each other, which simultaneously detect the radiation coming from the emitter according to two slightly different directions. Thus, possible zones remaining in the shadow with respect to one direction can generally be inspected by the other detector.

The invention will be now disclosed with reference to the accompanying drawings, relating to a preferred but non limiting embodiment of the invention itself, in which.

Figure 1:
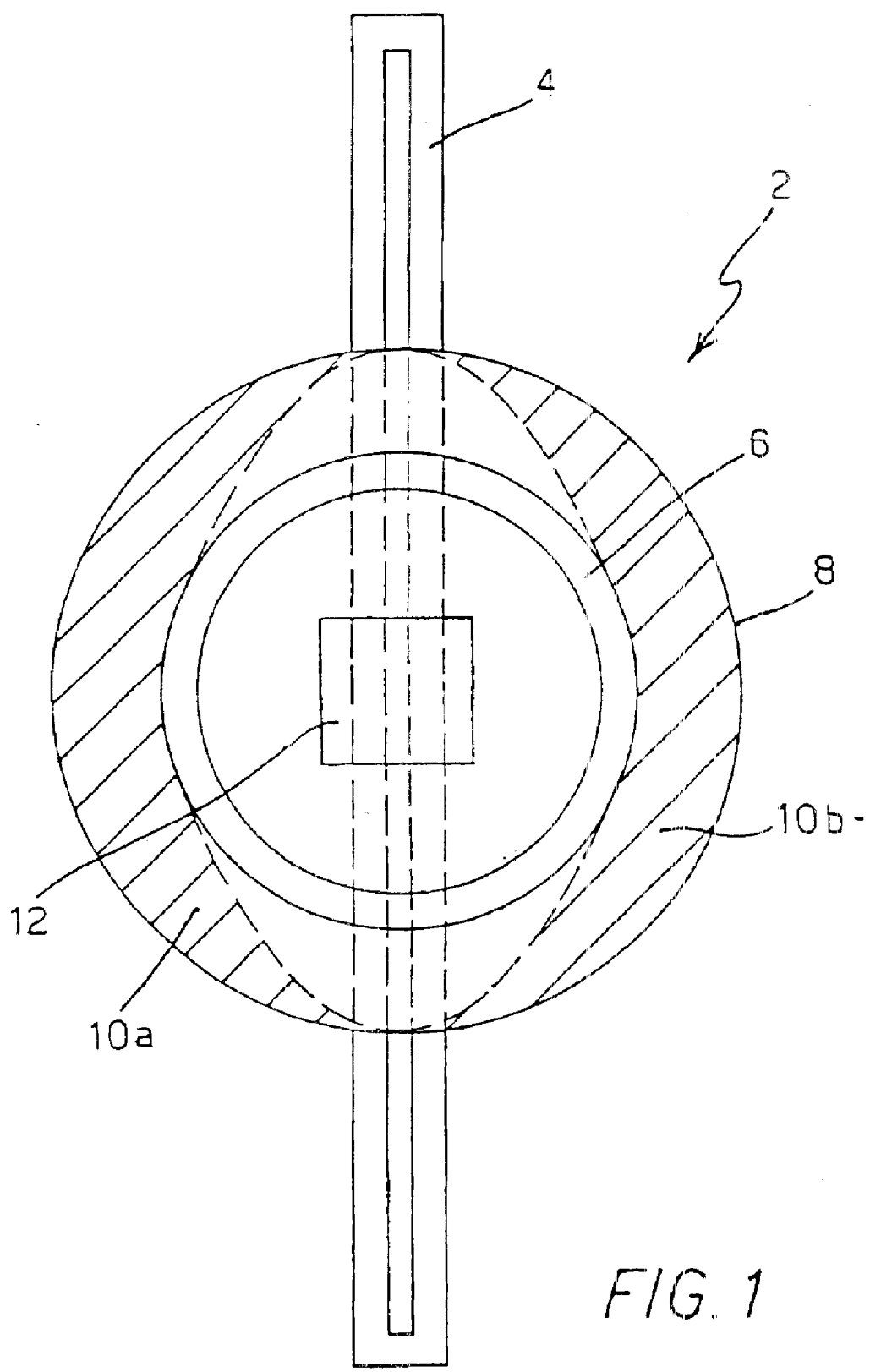
FIG. 1 is a schematic top view of a container in a prior art inspection device.

FIG. 1 shows, in a schematic top view, a container 2 passing, e.g. on a conveyor belt (not shown), in a known inspection device comprising a radiation emitter 12, located above container 2, and a linear radiation detector 4, located below the conveyor belt. The radiation beam emitted by emitter 12 passes through container 2 and its contents and arrives at detector 4, generating, thanks to known electronic processing means, an image related with the transparency, relative to the employed radiation, of the materials passed through by the beam.

Yet, as shown in the same FIG. 1, during displacement of container 2 inside the inspection device, the whole of the container bottom, where possible contaminants are deposited, is not properly inspected. In particular, dashed areas 10a, 10b remain excluded from inspection.

This mainly occurs because, in the container portion lying between neck 6 and external wall 8, the glass layer to be passed through is thicker, because of the wall inclination.

Even though the radiation beam emitted by emitter 12 is a divergent beam and penetrates into the container wholly irradiating the bottom area, linear detector 4 can only detect radiation lying in a vertical plane passing through its sensing surface, thus leaving lateral shadow zones 10a, 10b uncovered.

Figure 2:
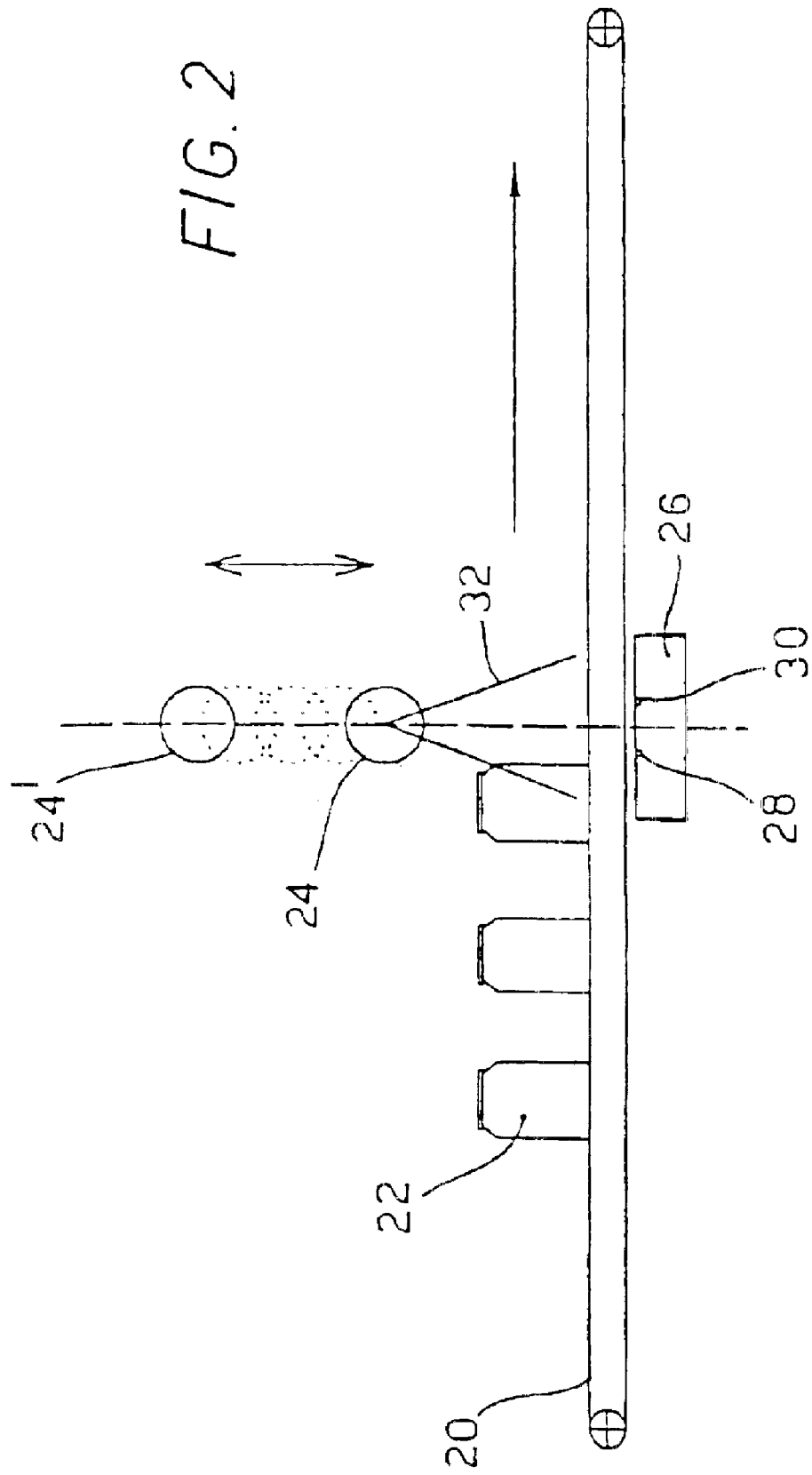
FIG. 2 is a schematic side view of an inspection device made in accordance with the invention.
Figure 3:
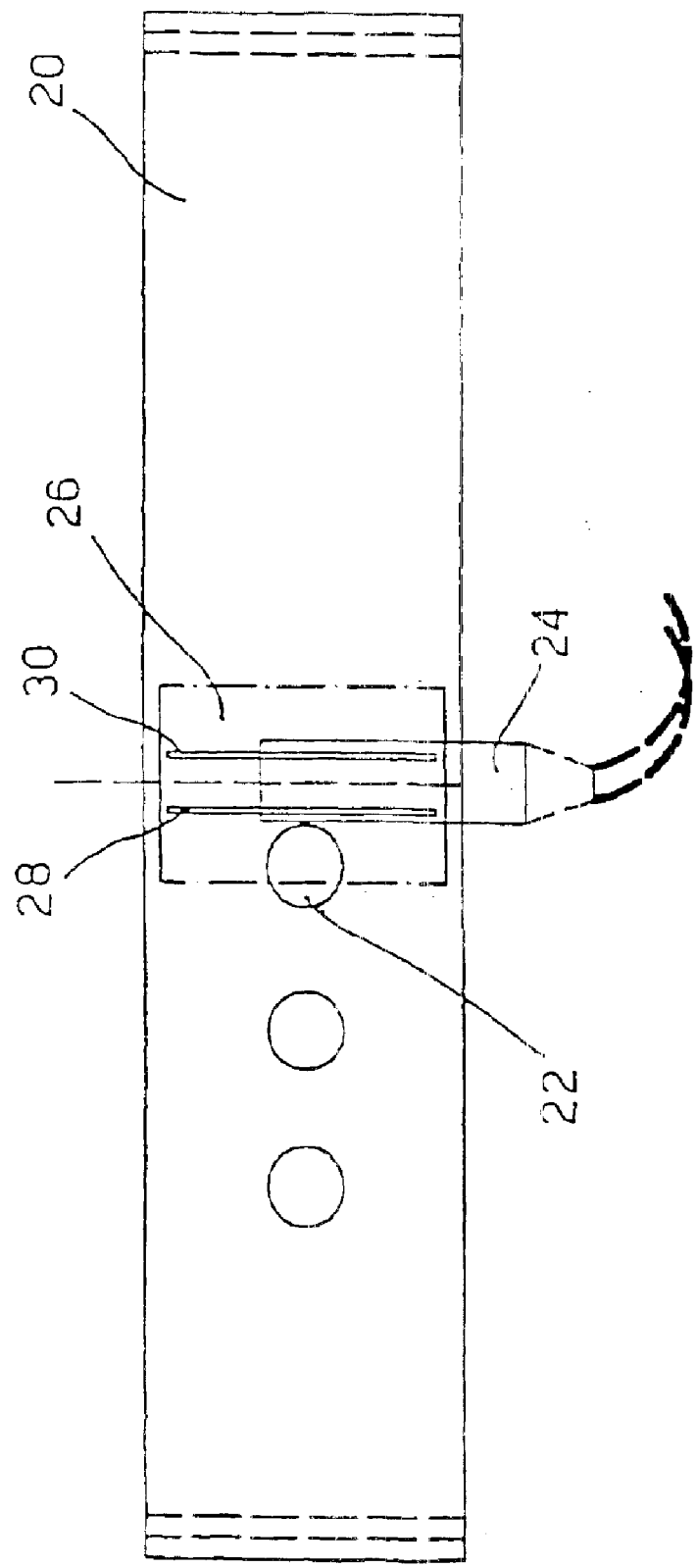
FIG. 3 is a top view of the inspection device shown in FIG. 2.
Figure 4:
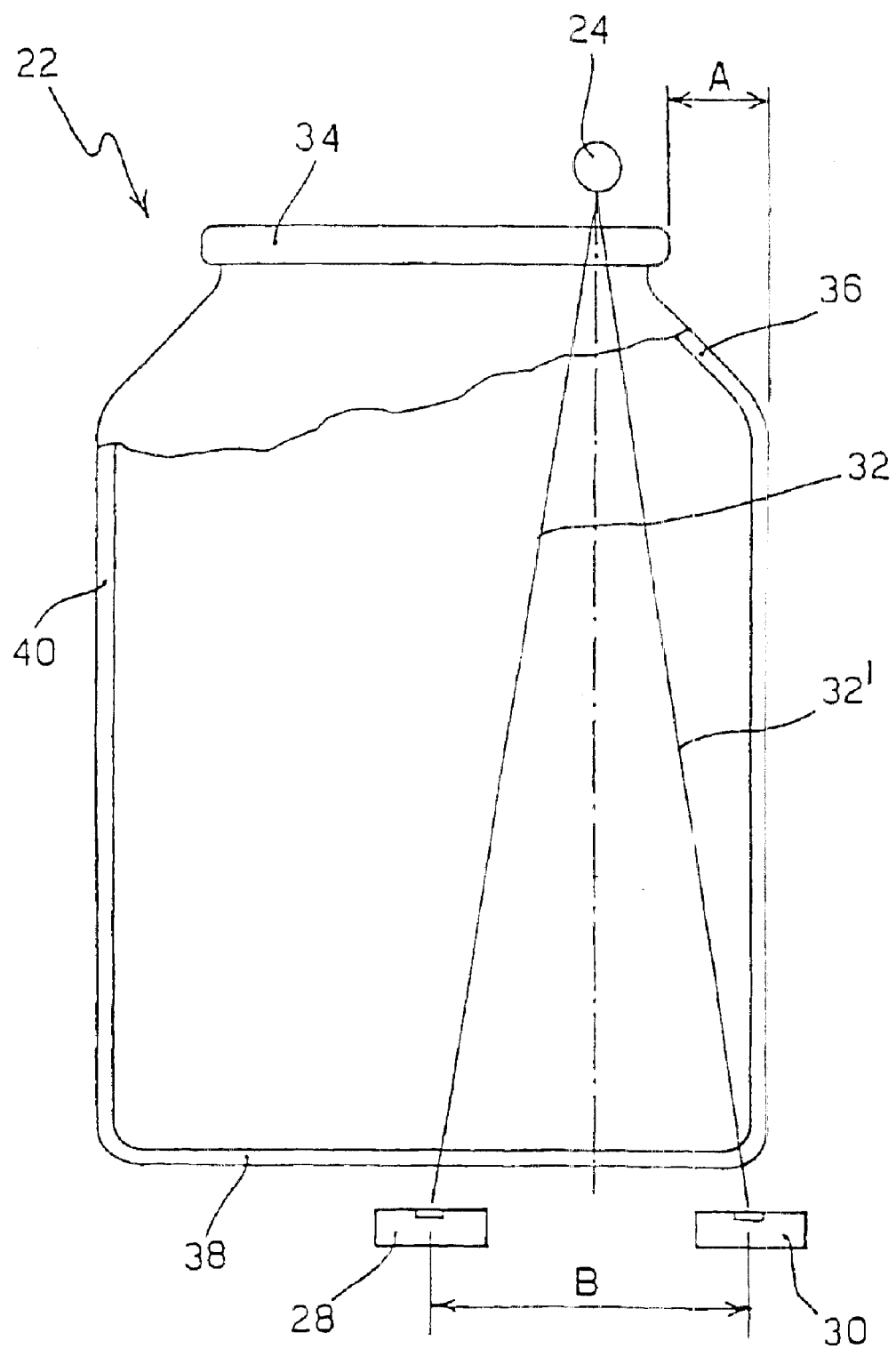
FIG. 4 is a schematic side view of a container during an inspection phase in an inspection device made in accordance with the invention.

An inspection device for containers of food and other products, made in accordance with the present invention, is instead disclosed referring to FIGS. 2, 3 and 4.

In particular, FIGS. 2 and 3 show a group of containers 22, e.g. foodstuff containing glass pots, which are conveyed by a conveyor belt 20 within a vertically arranged inspection device made in accordance with the present invention.

The inspection device comprise a radiation emitter 24, emitting a diverging ray beam 32, e.g. an X-ray beam, and means 26 adapted to detect the radiation emitted by emitter 24. The emitter position is vertically adjustable, e.g. between a low position 24 suitable for small size pots, and a high position 24', suitable for bottles or higher containers.

Actually, for an optimum operation of the device, as it will be disclosed in detail hereinafter with reference to FIG. 4, emitter 24 is to be located slightly above the neck of containers 22.

Radiation detecting means 26 comprise two distinct linear detectors 28, 30, slightly spaced and symmetrically located with respect to a vertical line passing through radiation emitter 24. Detectors 28, 30 receive radiation emitted by emitter 24 according to two different directions 32 and 32', as shown in detail in FIG. 4.

Actually FIG. 4 schematically shows an inspection phase of a pot 22, located between emitter 24, schematically shown above pot neck 34, and detectors 28 and 30. Reference symbol A in the drawing denotes the width of the inclined pot portion 36, between neck 34 and external wall 40. The drawing clearly shows that, if detectors 28, 30 are suitably spaced, the pot bottom, including the extreme bottom corners, can be wholly inspected.

Minimum spacing B between the detectors must at least be equal to twice the half-diameter difference A between neck 34 and external wall 40 of container of pot 22. Indeed in this way rays 32' emitted by emitter 24 penetrate inside container 22, without passing through inclined portion 36, and can pass, without obstacles, also through the bottom periphery, subsequently reaching detector 30. Similarly, the other end of bottom 38 of pot 22 is properly inspected by the other detector 28.

Moreover, to adapt the inspection device to containers with different shapes and sizes, the spacing between sensors 28 and 30 is made variable, of course always within the emission cone of emitter 24. Actually, to inspect wide bottom containers, a greater spacing between detectors 28 and 30 can be suitable, whereas in case of cylindrical container the detectors can be located closer to each other.

The apparatus of the invention thus allows improving the inspection phase of container of food products, ensuring a greater security and reliability. Moreover, the reduced size of the device allows employing it in place of single-detector devices of known type, in conventional vertical inspection apparatuses.

What is claimed is:

1. A device for non-destructive vertical inspection of containers of food products, for inspecting containers having a neck and a portion with inclined walls below said neck, the device comprising an emitter adapted to emit a radiation beam in a substantially vertical direction and means for detecting said radiation, said containers passing between said emitter and said radiation detecting means for being inspected, said radiation detecting means comprising two linear radiation detectors arranged substantially parallel to each other and spaced apart so as to receive radiation emitted by said emitter according to different directions characterized in that the spacing between said two radiation detectors can be adjusted so as to be equal to at least twice the half-diameter difference between said neck of the container and an external wall of the same container.

2. A device according to claim 1, wherein the spacing between said emitter and said two radiation detectors can be varied to suit the kinds and the shapes of the containers to be inspected.

3. A device according to claim 1 or 2, wherein the spacing between the two radiation detectors can be varied to suit the kind and the shape of the containers to be inspected.

4. A device according to claim 1, wherein the containers each have a diameter at the bottom of the container, and wherein said linear radiation detectors have a length greater than or equal to the diameter of the bottom of the containers to be inspected.

5. A method of using a device for non-destructive vertical X-ray inspection of containers of food products, for inspecting containers having a neck and a portion with inclined walls below said neck, the device comprising an emitter located slightly above the neck of the containers and adapted to emit a radiation beam in a substantially vertical direction, and means for detecting said radiation, said containers passing between said emitter and said radiation detecting means for being inspected in a substantially upright position, said radiation detecting means comprising two linear radiation detectors, arranged substantially parallel to each other and spaced apart so as to receive radiation emitted by said emitter according to different directions, characterised in that the spacing between said two radiation detectors is adjusted so as to remain equal to at least twice the half-diameter difference between the neck of the container and an external wall of the same container so that the zones remaining in the shadow created by the inclined wall portion with respect to one detector receiving the radiation according to one direction are simultaneously inspected by the other detector receiving the radiation according to a different direction, whereby the whole bottom of said container, including the extreme bottom corners is inspected.

6. A method according to claim 5, wherein the spacing between said emitter and said two radiation detectors is adjusted to suit the kinds and the shapes of the containers to be inspected.

7. A method according to any of preceding claims 5–6, wherein said linear radiation detectors have a length greater than or equal to the diameter of the bottom of the containers to be inspected.

* * * * *